United States Patent
Kato et al.

(10) Patent No.: US 8,920,822 B2
(45) Date of Patent: Dec. 30, 2014

(54) SKIN BEAUTIFIER

(75) Inventors: Ken Kato, Kawagoe (JP); Noriko Ueda, Kawagoe (JP); Susumu Miura, Kawagoe (JP); Toshimitsu Yoshioka, Kawagoe (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 0 days.

(21) Appl. No.: 12/947,891

(22) Filed: Nov. 17, 2010

(65) Prior Publication Data

US 2011/0065670 A1 Mar. 17, 2011

Related U.S. Application Data

(62) Division of application No. 10/594,661, filed as application No. PCT/JP2005/006030 on Mar. 30, 2005, now abandoned.

(30) Foreign Application Priority Data

Mar. 30, 2004 (JP) ................................. 2004-101142

(51) Int. Cl.
| | |
|---|---|
| *A61K 8/02* | (2006.01) |
| *A61Q 19/08* | (2006.01) |
| *A23J 7/00* | (2006.01) |
| *A23K 1/16* | (2006.01) |
| *A23L 1/30* | (2006.01) |
| *A61K 8/68* | (2006.01) |
| *A61K 31/688* | (2006.01) |
| *A61Q 19/00* | (2006.01) |

(52) U.S. Cl.
CPC . *A61Q 19/08* (2013.01); *A23J 7/00* (2013.01); *A23K 1/164* (2013.01); *A23L 1/30* (2013.01); *A23L 1/3006* (2013.01); *A61K 8/68* (2013.01); *A61K 31/688* (2013.01); *A61Q 19/00* (2013.01); *A23V 2002/00* (2013.01); *A61K 2800/92* (2013.01)
USPC ........................................................ 424/401

(58) Field of Classification Search
None
See application file for complete search history.

(56) References Cited

U.S. PATENT DOCUMENTS

| 7,511,010 | B2 | 3/2009 | Msika et al. | |
|---|---|---|---|---|
| 2006/0128666 | A1* | 6/2006 | Nieuwenhuizen | ............... 514/78 |
| 2006/0134182 | A1* | 6/2006 | Nieuwenhuizen | ............ 424/442 |
| 2006/0240115 | A1 | 10/2006 | Kanamaru et al. | |

FOREIGN PATENT DOCUMENTS

| FR | 2692781 | A1 | 12/1993 | |
|---|---|---|---|---|
| JP | 8259988 | A | 10/1996 | |
| JP | 8310938 | A | 11/1996 | |
| JP | 9208419 | A | 8/1997 | |
| JP | 11269074 | A | 10/1999 | |
| JP | 2001128642 | A | 5/2001 | |
| JP | 2001158735 | A | 6/2001 | |
| JP | 2001158736 | A | 6/2001 | |
| JP | 2002226394 | A | 8/2002 | |
| JP | 2002536336 | A | 10/2002 | |
| JP | 2003146883 | A | 5/2003 | |
| JP | 2003252765 | A | 9/2003 | |
| WO | 2004064819 | A1 | 8/2004 | |
| WO | WO2005/030161 | * | 4/2005 | ............... A61K 7/48 |

OTHER PUBLICATIONS

Nordhauser et al., Sterilization of Drugs and Devices (Preface), Interpharm Press, 1998.*
Graves et al., "Sphingomyelin: A Potentially Beneficial Component of Milk Fat", http://www.livestocktrail.illinois.edu/dairynet/paperDisplay.cfm?ContentID=6564, accessed Feb. 21, 2014.*
Zeisel et al. Choline, Phosphatidylcholine and Sphingomyelin in Human and Bovine Milk and Infant Formulas, J Nutr, 1986, pp. 50-58.*
Milk Nutrition Facts, Food and Nutrition Service, USDA (2007).
Hubert Vesper et al., "Sphingolipids in Food and the Emerging Importance of Sphingolipids to Nutrition," 1999, pp. 1239-1250, vol. 129, No. 7, Journal of Nutrition.
Foerster, Thomas, "Cosmetic Lipids and the Skin Barrier," 2002, pp. 102-105, XP 002532668, Informa Health Care.
Kabara, Jon J. et al., "Preservative-Free and Self-Preserving Cosmetics and Drugs: Principles and Practices," 1997, pp. 141-143, XP002532669, CRC Press.
Supplementary European Search Report mailed Jun. 30, 2009, received in corresponding European Patent Application No. 05 72 7923.
Office Action issued on Sep. 15, 2009, in copending Japanese Patent Application No. 2004-101142.

* cited by examiner

*Primary Examiner* — Kortney L Klinkel
*Assistant Examiner* — Melissa Javier
(74) *Attorney, Agent, or Firm* — Sughrue Mion, PLLC

(57) ABSTRACT

A skin beautifier contains sphingomyelin, which is a phospholipid, as an effective ingredient. In addition, skin-beautifying food or feed contains sphingomyelin as an effective ingredient. The present invention provides a skin beautifier and skin-beautifying food or feed supplying effects on beauty, such as skin-moisturizing and protecting effects, skin-roughness-preventing and improving effects, and a wrinkle-preventing effect, by oral ingestion thereof.

4 Claims, No Drawings

SKIN BEAUTIFIER

CROSS REFERENCE TO A RELATED APPLICATIONS

This is a divisional patent application of application Ser. No. 10/594,661 filed Sep. 9, 2006, now pending.

TECHNICAL FIELD

The present invention relates to a skin beautifier containing sphingomyelin as an effective ingredient and providing beauty effects, such as skin-moisturizing, skin-beautifying, skin-roughness-preventing, and wrinkle-preventing effects, by oral ingestion thereof, and relates to a skin-beautifying food/drink and a feed containing sphingomyelin.

BACKGROUND ART

The skin is an interface of an organism with the environment, prevents moisture loss from the body, and has a skin barrier function preventing the invasion of biotoxic substances, such as microorganisms and allergens, from the environment. Intercorneocyte lipids, ceramides in particular, and sebum in the stratum corneum are said to bear these functions. It is said that the stratum corneum must contain 10 to 20% moisture to function normally and maintain a healthy condition. The moisture is retained in the stratum corneum by the skin barrier function and flexibility and elasticity of the skin are thereby maintained.

When the moisture in the stratum corneum decreases, the stratum corneum loses the flexibility and is hardened. This causes chapping. In so-called roughened skin, i.e., a condition that the dermatoglyphic patterns disappear or are unclear, a significant decrease in the moisture content is observed in the stratum corneum. Roughened skin is not only a cosmetic problem of poor appearance but also a preliminary stage causing a skin disease, and has a pathological meaning. In addition, improvement of roughened skin makes a dried skin surface soft and smooth and further leads to an improvement of fine wrinkles.

It is known that when the skin barrier function of the stratum corneum decreases, the loss of moisture from the skin is serious compared with that in a healthy condition. In addition, an increase in transepidermal water loss (TEWL) through the skin is observed. This TEWL is closely involved in the barrier function and the moisturizing function of the stratum corneum and is used as an indicator of the skin barrier function.

Therefore, a healthy condition of the skin, i.e., a beautified skin condition, can be achieved by increasing the moisture content of the skin or suppressing an increase in TEWL.

Furthermore, recently, it has become a problem in animals, particularly in pets, that skin conditions are aggravated by influence of allergy or the like. The skin conditions can be improved and healthy skin conditions can be realized by moisturizing and protecting the skin.

Ceramides are one of human skin components and have skin-moisturizing and protecting functions and skin-roughness-preventing and improving effects. As cosmetics utilizing ceramides, skin cosmetic products containing a member of ceramide family, such as ceramides, glucosylceramides, and galactosylceramides, and diisopropylamine dichloroacetate or γ-aminobutyric acid are known (Patent Document 1). However, there are problems such that ceramides applied to the skin cannot reach nor be absorbed in the skin due to a barrier of epidermal lipids and that cosmetic ingredients other than ceramides cause irritation and inflammation.

In addition, health foods containing ceramides composed of sphingosine, a fatty acid, and a sugar, as an effective ingredient are also known (Patent Document 2). As the raw materials for the ceramides, composed of sphingosine, a fatty acid, and a sugar, those derived from Amorphophalus konjac and rice are commercially available. However, these raw materials contain ceramides in a low amount less than 3%. Therefore, in order to achieve the effects by oral ingestion, it is necessary to blend a large amount of the raw materials. In addition, since their prices are high, the health foods are unsatisfactory. Therefore, materials which can be readily ingested from daily food are desired.

Sphingomyelin accounts for about 30% of phospholipids in milk and has a structure in which phosphocholine is bonded to a ceramide skeleton composed of sphingosine and a fatty acid. Sphingomyelin is known to be present in the brain and nerve tissues in large amounts (Non-Patent Document 1). It is also known that sphingomyelin is slightly contained in food such as yolk.

It is reported that a sphingomyelin is absorbed through the small intestine in blood vessels when orally ingested (Non-Patent Document 2). In addition, it is known that a sphingomyelin in the stratum glanulosum of the skin is hydrolyzed by sphingomyelinase into a ceramide to be supplied to the stratum corneum (Non-Patent Document 3).

However, it has not been reported that the oral ingestion of a sphingomyelin can provide beauty effects, such as skin-moisturizing and protecting effects, skin-roughness-preventing and improving effects, and a wrinkle-preventing effect.

[Patent Document 1]: Japanese Patent Laid-Open No. Hei 01-22810
[Patent Document 2]: Japanese Patent Laid-Open No. Hei 11-113530
[Non-Patent Document 1]: Harper's Biochemistry, 24th Ed. 1997, 162.
[Non-Patent Document 2]: Schmelz, et al. J. Nutr. 1994, 124, 702-712.
[Non-Patent Document 3]: Uchida, et al. Seikagaku (The Journal of Japanese Biochemical Society) 2001, 73(4), 269-272.

It is an object of the present invention to provide a skin beautifier which has beauty effects, such as skin-moisturizing and protecting effects, skin-roughness-preventing and improving effects, and a wrinkle-preventing effect, by oral ingestion thereof and which contains a safe raw material derived from food as an effective ingredient. In addition, it is an object of the present invention to provide a skin-beautifying food or feed which has beauty effects, such as skin-moisturizing and protecting effects, skin-roughness-preventing and improving effects, and a wrinkle-preventing effect, by oral ingestion thereof and which includes a safe raw material derived from food.

DISCLOSURE OF THE INVENTION

In view of the aforementioned problems, the present inventors have conducted intensive searching for a component which has beauty effects, such as skin-moisturizing and protecting effects, skin-roughness-preventing and improving effects, and a wrinkle-preventing effect, by oral ingestion thereof, and have found that beauty effects, such as skin-moisturizing and protecting effects, skin-roughness-preventing and improving effects, and a wrinkle-preventing effect, can be obtained by orally ingesting a sphingomyelin, which is a phospholipid. In addition, the present inventors have found that this sphingomyelin can be utilized as an effective ingredient of a skin beautifier and further found that sphingomyelin can be blended with a food or feed to provide a skin-beautifying food or feed. Thus, the present invention has been accomplished. The skin-beautifying feed in the present invention refers to the feed which exerts having skin-moisturizing and protecting effects in an animal to improve a skin condition thereof.

ADVANTAGES OF THE INVENTION

According to the present invention, a skin beautifier containing a sphingomyelin as an effective ingredient and a skin-beautifying food or feed containing a sphingomyelin can be provided. Since the effective ingredient of the skin beautifier according to the present invention is derived from food, the skin beautifier is safe and can achieve the beauty effects, such as skin-moisturizing and protecting effects, skin-roughness-preventing and improving effects, and a wrinkle-preventing effect, by oral ingestion thereof.

BEST MODE FOR CARRYING OUT THE INVENTION

The present invention is characterized by using a sphingomyelin, a phospholipid, as an effective ingredient. Sphingomyelins which can be used in the present invention are derived from natural substances. For example, sphingomyelins derived from milk such as cow milk and goat milk and egg yolk of hens can be used. Actually, an inexpensive sphingomyelin raw material derived from cow milk, which contains sphingomyelins in a high concentration of 25% or more, is available at a market. Such a raw material may be advantageously used.

In the present invention, the above-mentioned sphingomyelin may be used as a skin beautifier without modification or may be used as a nutrition composition by blending the sphingomyelin with raw materials, such as sugars, lipids, proteins, vitamins, minerals, and flavorings which are generally used in medicines, food, and feed. In addition, the sphingomyelin may be formulated into powder, granules, tablets, capsules, or drink according to a known method. Furthermore, other components having an effect on beauty, for example, collagen which accelerates collagen production in the skin, vitamin C, or iron, can be used with the sphingomyelin.

With respect to the effective dose of the skin beautifier according to the present invention, it was confirmed by an animal study using nude mice described below that the moisture content of the skin was increased and the transepidermal water loss (TEWL) through skin was decreased by oral administration of 2 mg or more, preferably 5 mg or more, of sphingomyelin per kg of mouse body weight. Therefore, generally, the beauty effects, such as skin-moisturizing and protecting effects, skin-roughness-preventing and improving effects, and a wrinkle-preventing effect, can be expected by administration of 2 mg or more, preferably 5 mg or more of sphingomyelin per day for an adult. Therefore, this amount may be necessarily ingested.

Additionally, in the skin-beautifying food according to the present invention, sphingomyelin may be blended with general food, for example, yogurt, milk-based drink, wafers, or dessert. With respect to the skin-beautifying food, though it depends on the form of the food, 100 g of the food preferably contains 0.1 to 400 mg of sphingomyelin in order to administer 2 mg or more of sphingomyelin per day for an adult.

Furthermore, in the skin-beautifying feed according to the present invention, sphingomyelin may be blended with general feed, for example, livestock feed or pet food. With respect to the skin-beautifying feed, 100 g of the feed preferably contains 0.1 to 400 mg of sphingomyelin in order to administer 2 mg or more of sphingomyelin per day.

In the present invention, the method for blending the sphingomyelin is not specifically limited. For example, when sphingomyelin is added to or blended in a solution, sphingomyelin may be used after prepared into a form of a medicine, food, or feed by suspending or dissolving a sphingomyelin raw material in deionized water and stirring and mixing the resulting mixture. The stirring and mixing may be conducted under any conditions as long as sphingomyelin can be uniformly mixed, and may be conducted with an ultradisperser or a TK homomixer. This sphingomyelin solution may be concentrated by using an RO membrane or may be dried by lyophilization, if necessary, in order to be readily used for a medicine, food, or feed.

In the present invention, sterilization procedures which are generally conducted in the manufacturing of a medicine, food, or feed can be employed. If a product is in a form of powder, dry-heat sterilization can be also employed. Therefore, according to the present invention, a medicine, food, and feed containing the sphingomyelin can be manufactured in various forms such as a solution, gel, powder, or granules.

Effects of the skin beautifier according to the present invention were investigated by an animal test using nude mice.

(Preparation of Feed)

A sphingomyelin raw material (Phospholac 500; manufactured by NZMP) containing 10% of sphingomyelins was dissolved in deionized water as shown in Table 1. The solution was heated to 50° C. and then mixed under stirring with an ultradisperser (ULTRA-TURRAX T-25; manufactured by IKA Japan) at 9500 rpm for 20 minutes to prepare Test Feeds 1 to 3.

TABLE 1

| Feed | Sphingomyelin Content (mg/100 g) | Sphingomyelin Raw Material (g) | Deionized Water (g) |
|---|---|---|---|
| 1 | 20 | 2 | 998 |
| 2 | 50 | 5 | 995 |
| 3 | 100 | 10 | 990 |

(Animal Test)

Five-week old CD-1 (ICR)-nu/nu mice were divided into the following 4 test groups (10 mice in each group), namely, (Group A) a group receiving 10 g of physiological saline per kg of mouse body weight, (Group B) a group receiving 10 g of the Test Feed 1 per kg of mouse body weight, (Group C) a group receiving 10 g of the Test Feed 2 per kg of mouse body weight, and (Group D) a group receiving 10 g of the Test Feed 3 per kg of mouse body weight. Mice in all the groups were fed by orally administering the feed once daily by gavage feeding for 4 weeks. Moisture contents and transepidermal water losses in the tail skin of each mouse were measured at the start and the end of the feeding. Values at the end of the feeding (rates of increase) were calculated by assuming each of the values at the start of the feeding to be 100. The moisture contents of the skin and the transepidermal water losses were measured using Corneometer and Tewameter, respectively, which were manufactured by Courage+Khazaka. Table 2 shows the results.

TABLE 2

| Group | Administered Sphingomyelin Amount (mg/kg) | Increase Rate of Moisture (%) | Increase Rate of Transepidermal Water Loss (%) |
|---|---|---|---|
| A | 0 | 109 | 172 |
| B | 2 | 155 | 152 |
| C | 5 | 245 | 137 |
| D | 10 | 253 | 140 |

With reference to the results shown in Table 2, in Group A the moisture content of the skin after 9-week administration hardly changed, but the contents increased by about 1.5 times in Group 13 and by about 2.5 times in Groups C and D. The transepidermal water loss after 4-week administration increased by about 1.7 times in Group A, but increased only by about 11.5 times in Group B and by about 1.4 times in Groups C and D. Hence, it was confirmed that the moisture content of the skin is increased and the transepidermal water loss is decreased by oral administration of the sphingomyelin. These effects were observed by administering 2 mg or more sphingomyelin per kg of mouse body weight, and further the effects were significant by administering 5 mg or more of sphingomyelin per kg of mouse body weight.

The present invention will now be described in detail with reference to examples, but these examples are only exemplary embodiments of the present invention. The present invention is not limited to these examples.

Example 1

A reaction solution prepared by adding protease to an aqueous solution containing 10% of whey protein concentrate (WPC) was extracted with a solution of chloroform-methanol (2:1). The extract was concentrated and then was further extracted with acetone to obtain a complex lipid fraction. Then, this complex lipid fraction was subjected to a florisil-column chromatography and eluted successively with chloroform-methanol solutions to obtain a fraction containing phospholipid. This phospholipid fraction was subjected to a silica-gel chromatography and eluted successively with chloroform-methanol solutions to obtain a fraction phospholipid. This fraction was lyophilized to obtain a sphingomyelin raw material. This sphingomyelin raw material was developed on a thin-layer chromatography, followed by color development with the Dittmer reagent. The sphingomyelin content was measured by densitometry to be 95.2%. This sphingomyelin raw material can be used as a skin beautifier according to the present invention without modification.

Example 2

Raw materials were mixed at the blending quantities shown in Table 3, and then were made into tablets each weighing 1 g by a known method to manufacture the skin beautifier according to the present invention.

TABLE 3

| Hydrous crystalline glucose | 83.5 (% by weight) |
|---|---|
| Sphingomyelin raw material (content: 10%, Phospholac 500 manufactured by NZMP) | 10.0 |
| Mineral mixture | 5.0 |
| Sugar ester | 1.0 |
| Flavoring | 0.5 |

In 1 g of this skin beautifier, 10 mg of sphingomyelin was contained.

Example 3

Fifty grams of a sphingomyelin raw material (α-Lipid; manufactured by NZMP) containing 25% of sphingomyelin was dissolved in 4950 g of deionized water. The solution was heated to 50° C. and then mixed under stirring with a TK homomixer (TK ROBOMICS; manufactured by Tokushu Kika Kogyo) at 6000 rpm for 30 minutes to prepare a sphingomyelin solution containing sphingomyelin at 250 mg/100 g solution. This sphingomyelin solution (4.0 kg) was blended with 5.0 kg of casein, 5.0 kg of soy protein, 1.0 kg of fish oil, 3.0 kg of perilla oil, 18.0 kg of dextrin, 6.0 kg of mineral mixture, 1.95 kg of vitamin mixture, 2.0 kg of an emulsifier, 4.0 kg of a stabilizer, and 0.05 kg of flavoring, and the mixture was packed in 200-ml retort pouches. Then, sterilization by a retort sterilizer (First-class pressure vessel, TYPE: RCS-4CRTGN; manufactured by HISAKA WORKS) at 121° C. for 20 minutes was performed to manufacture 50 kg of a skin-beautifying liquid nutrition composition according to the present invention. In 100 g of this skin-beautifying liquid nutrition composition, 20 mg of sphingomyelin was contained.

Example 4

Ten grams of a sphingomyelin raw material (Phospholac 500; manufactured by NZMP) containing 10% of sphingomyelin was dissolved in 700 g of deionized water. The solution was heated to 50° C. and then mixed under stirring with an ultradisperser (ULTRA-TURRAX T-25; manufactured by IKA Japan) at 9500 rpm for 30 minutes. To this solution, 40 g of sorbitol, 2 g of an acidifier, 2 g of flavoring, 5 g of pectin, 5 g of whey protein concentrate, 1 g of calcium lactate, and 235 g of deionized water were added. The mixture was stirred and mixed and then was packed in 200-ml pouches with a screw cap. After the sterilization at 85° C. for 20 minutes, the packs were hermetically sealed to prepare 5 bags (each 200 g) of skin-beautifying gel-type food according to the present invention. No precipitate was observed and no abnormal flavor was detected in all thus obtained skin-beautifying gel-type food. In 100 g of this skin-beautifying gel-type food, 100 mg of sphingomyelin was contained.

Example 5

Two grams of an acidifier was dissolved in 700 g of deionized water, and in this solution, 10 g of a sphingomyelin raw material (α-Lipid; manufactured by NZMP) containing 25% of sphingomyelin was dissolved. The solution was heated to 50° C. and then mixed under stirring with an ultradisperser (ULTRA-TURRAX T-25 manufactured by IKA Japan) at 9500 rpm for 30 minutes. To this solution, 100 g of maltitol, 20 g of reduced glucose, 2 g of flavoring, and 166 g of deionized water were added. The mixture was packed in 100-ml glass bottles and was sterilized at 90° C. for 15 minutes. Then, the bottles were hermetically sealed to prepare 10 bottles (each 100 ml) of skin-beautifying drink according to the present invention. No precipitate was observed and no abnormal flavor was detected in all thus obtained skin-beautifying drink. In 100 g of this skin-beautifying drink, 250 mg of sphingomyelin was contained.

Example 6

Two kilograms of a sphingomyelin raw material (SM-4; manufactured by Corman) containing 4% of sphingomyelin was dissolved in 98 kg of deionized water. The solution was heated to 50° C. and then was mixed under stirring with a TK homomixer (MARK II 160 type; manufactured by Kokusyu Kika Kogyo) at 3600 rpm for 40 minutes to prepare a sphingomyelin solution containing sphingomyelin at 80 mg/100 g solution. This sphingomyelin solution (10 kg) was blended with 12 kg of soybean cake, 14 kg of skimmed milk powder, 4 kg of soybean oil, 2 kg of corn oil, 23.2 kg of palm oil, 14 kg of corn starch, 9 kg of flour, 2 kg of bran, 5 kg of a vitamin mixture, 2.8 kg of cellulose, and 2 kg of a mineral mixture. The mixture was sterilized at 120° C. for 4 minutes to prepare 100 kg of skin-beautifying dog food according to the present invention. In 100 g of this skin-beautifying dog food, 8 mg of sphingomyelin was contained.

INDUSTRIAL APPLICABILITY

The skin beautifier according to the present invention is safe because the effective ingredient is derived from food, and provides beauty effects, such as skin-moisturizing and protecting effects, skin-roughness-preventing and improving effects, and a wrinkle-preventing effect, by oral ingestion thereof.

The invention claimed is:

1. A method of moisturizing mammalian skin by decreasing transepidermal water loss comprising the step of a mammal in need thereof orally ingesting 2 mg or more of sphingomyelin per kg of the mammal's body weight.

2. The method of moisturizing mammalian skin of claim 1, comprising the mammal in need thereof ingesting 5 mg or more of sphingomyelin per kg of the mammal's body weight.

3. The method of moisturizing mammalian skin of claim 1, wherein the sphingomyelin is mixed in a food, feed or medicine.

4. The method of moisturizing mammalian skin of claim 2, wherein the sphingomyelin is mixed in a food, feed or medicine.

* * * * *